(12) United States Patent
Huh (10) Patent No.: US 11,439,538 B2
(45) Date of Patent: Sep. 13, 2022

(54) PROTECTOR FOR WELDER

(71) Applicant: OTOS WING.CO., LTD., Seoul (KR)

(72) Inventor: Moon Young Huh, Seoul (KR)

(73) Assignee: OTOS WING.CO., LTD., Seoul (KR)

( * ) Notice: Subject to any disclaimer, the term of this patent is extended or adjusted under 35 U.S.C. 154(b) by 660 days.

(21) Appl. No.: 16/128,149

(22) Filed: Sep. 11, 2018

(65) Prior Publication Data

US 2019/0076297 A1    Mar. 14, 2019

(30) Foreign Application Priority Data

Sep. 12, 2017  (KR) ........................ 10-2017-0116669

(51) Int. Cl.
*A61F 9/06* (2006.01)
*G02B 27/01* (2006.01)
*B23K 9/32* (2006.01)

(52) U.S. Cl.
CPC .......... *A61F 9/067* (2013.01); *G02B 27/0172* (2013.01); *B23K 9/322* (2013.01); *G02B 2027/0141* (2013.01); *G02B 2027/0156* (2013.01); *G02B 2027/0159* (2013.01); *G02B 2027/0167* (2013.01)

(58) Field of Classification Search
CPC ........................... A61F 9/067; G02B 27/0172
USPC ......................... 2/8.2, 8.4, 8.7, 8.8
See application file for complete search history.

(56) References Cited

U.S. PATENT DOCUMENTS

| 6,227,667 | B1 | 5/2001 | Halldorsson et al. |
| 8,457,949 | B2 | 6/2013 | Huh |
| 2008/0158502 | A1 | 7/2008 | Becker et al. |
| 2011/0083241 | A1 | 4/2011 | Cole |
| 2015/0209887 | A1 | 7/2015 | DeLisio |
| 2016/0163221 | A1 | 6/2016 | Sommer et al. |
| 2017/0173720 | A1 | 6/2017 | Sumner |

FOREIGN PATENT DOCUMENTS

| DE | 196 31 414 A1 | 2/1998 |
| EP | 3192481 A1 | 7/2017 |
| JP | 2013-504437 A | 2/2013 |
| KR | 10-1145236 B1 | 5/2012 |

OTHER PUBLICATIONS

First Examination Report dated May 28, 2019 for German Patent Appln. No. 10 2018 215, 8 pages.
Search Report and Written Opinion from the Direction De La Propriete Industrielle for FR1858077 dated Oct. 22, 2020, all pages.
Office Action for Korean Application No. 10-2017-1166669 dated Aug. 7, 2018, 4 pages.

*Primary Examiner* — Alissa J Tompkins
*Assistant Examiner* — Brieanna Szafran
(74) *Attorney, Agent, or Firm* — Kilpatrick Townsend & Stockton LLP (57) ABSTRACT

A protector for a welder includes a main body configured to cover a face and eyes of an operator; a darkening filter arranged in a front side of the main body and configured to protect the eyes of the operator; an image generator arranged in the main body and configured to generate image light; an optical path bender configured to change a proceeding path of the image light; and a combiner configured to generate a virtual image on an outer portion of the main body by projecting the image light, and arranged adjacent to the darkening filter.

9 Claims, 9 Drawing Sheets

PROTECTOR FOR WELDER

CROSS-REFERENCE TO RELATED APPLICATION

This application claims the benefit of Korean Patent Application No. 10-2017-0116669, filed on Sep. 12, 2017, in the Korean Intellectual Property Office, the disclosure of which is incorporated herein in its entirety by reference.

BACKGROUND

1. Field

One or more embodiments relate to a protector for a welder.

2. Description of the Related Art

An operator wears a protector for protection from light and high temperature heat generated during a welding process such as arc welding. While the operator wears the protector, the operator may only check processing of the welding through the protector, and thus, the operator has to remove the protector and check with the naked eye in order to identify various information for the welding operation, such as conditions set in a welding apparatus.

SUMMARY

One or more embodiments include a protector for a welder.

Additional aspects will be set forth in part in the description which follows and, in part, will be apparent from the description, or may be learned by practice of the presented embodiments.

According to one or more embodiments, a protector for a welder, the protector includes: a main body configured to cover a face and eyes of an operator; a darkening filter arranged in a front side of the main body and configured to protect the eyes of the operator; an image generator arranged in the main body and configured to generate image light; an optical path bender configured to change a proceeding path of the image light; and a combiner configured to generate a virtual image on an outer portion of the main body by projecting the image light, and arranged adjacent to the darkening filter.

The optical path bender may include at least one of a reflective mirror, a semi-transmissive mirror, and optical fiber.

The virtual image may represent information based on at least one of information about electric power used during a welding operation or information about a welding wire.

The protector may further include a combiner mover configured to move the combiner, so that the combiner is located in the main body without overlapping with the darkening filter in a first mode and the combiner overlaps with at least a part of the darkening filter in a second mode.

The protector may further include a controller configured to control a location of the virtual image.

The controller may be configured to control the location of the virtual image by changing a location of at least one of the image generator or the optical path bender.

The protector may further include a mover configured to move the location of at least one of the image generator or the optical path bender.

The controller may be configured to control the location of the virtual image based on a size of an image generated by the image generator.

The virtual image may have a brightness that is based on a darkness of the darkening filter or a brightness inside the main body.

The protector may further include an optical sensor arranged in the main body.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

The exemplary embodiments will be described below in more detail with reference to the accompanying drawings. Those components that are the same or are in correspondence are rendered the same reference numeral regardless of the figure number, and redundant explanations are omitted.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

It will be understood that when a region, or component is referred to as being "formed on" another layer, region, or component, it may be directly or indirectly formed on the other layer, region, or component. That is, for example, intervening regions, or components may be present.

Sizes of components in the drawings may be exaggerated for convenience of explanation. In other words, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

In the embodiments below, it will be understood when areas or elements or the like are referred to as being "connected," they may be directly connected or an intervening portion may be present between areas or elements. For example, when areas or elements or the like are referred to as being "electrically connected," they may be directly electrically connected, or areas or elements may be indirectly electrically connected and an intervening portion may be present. As used herein, the term "and/or" includes any and all combinations of one or more of the associated listed items. Expressions such as "at least one of," when preceding a list of elements, modify the entire list of elements and do not modify the individual elements of the list.

Figure 1:
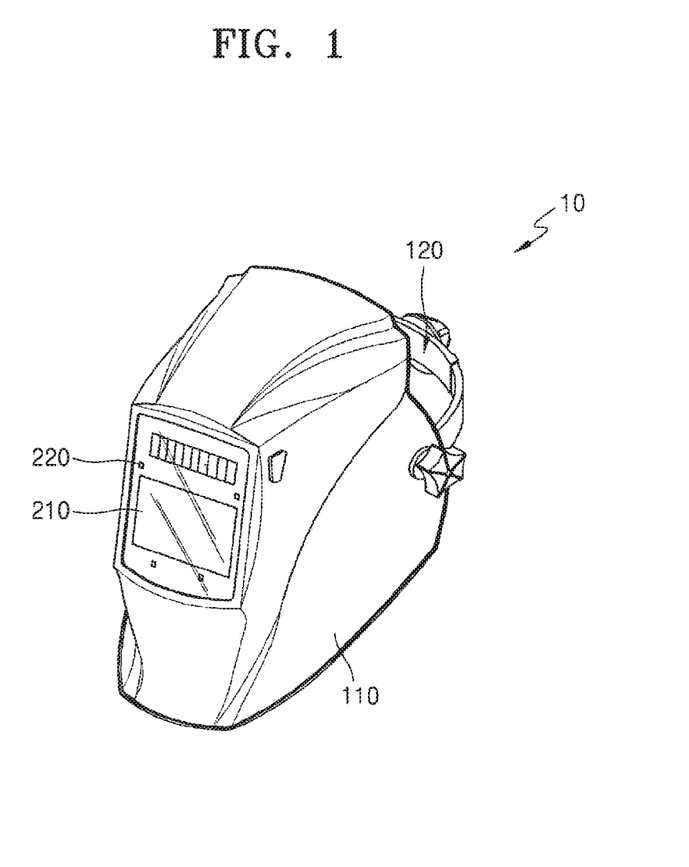
FIG. 1 is a perspective view of a protector for a welder according to an embodiment.

FIG. 1 is a perspective view of a protector 10 for a welder according to an embodiment.

Referring to FIG. 1, the protector 10 may include a main body 110 protecting the face and the eyes of an operator, and a fixing portion 120 arranged on a rear surface of the main body 110 to fix the protector 10 to a head portion of the operator. The main body 110 may include a material having a predetermined strength, e.g., reinforced plastic, but is not limited thereto, that is, may include various materials having resistance against such elements as sparks that may generate during a welding operation. The fixing portion 120 directly may contact the head of the operator, and thus, a side surface of the fixing portion 120, that is, at least a part of an internal surface directly contacting the head of the operator, may include a soft material such as fiber or cushion material.

The main body 110 is a main part of the protector 10, and a darkening filter 210 may be arranged in a front surface of the main body 110.

The darkening filter 210 blocks welding light generated when the operator performs a welding operation, to protect the eyes of the operator. The darkening filter 210 may include, for example, a liquid crystal display (LCD) panel, a darkness (or a lightness) of which may be adjusted according to an orientation direction of liquid crystal. As an embodiment, the darkness of the darkening filter 210 may be manually adjusted according to a selection (request) of the operator. Alternatively, the darkness of the darkening filter 210 may be automatically adjusted according to the brightness of the welding light. When the darkness is automatically adjusted according to the brightness of the welding light, a first optical sensor 220 may be used. For example, when the first optical sensor 220 senses the intensity of the welding light and transfers the sensed intensity as a predetermined electric signal to a controller that will be described later, the controller may control the darkness of the darkening filter 210 based on the intensity of the welding light. FIG. 1 shows that the first optical sensor 220 is arranged in the front surface of the main body 110, for example, around the darkening filter 210.

Figure 2:
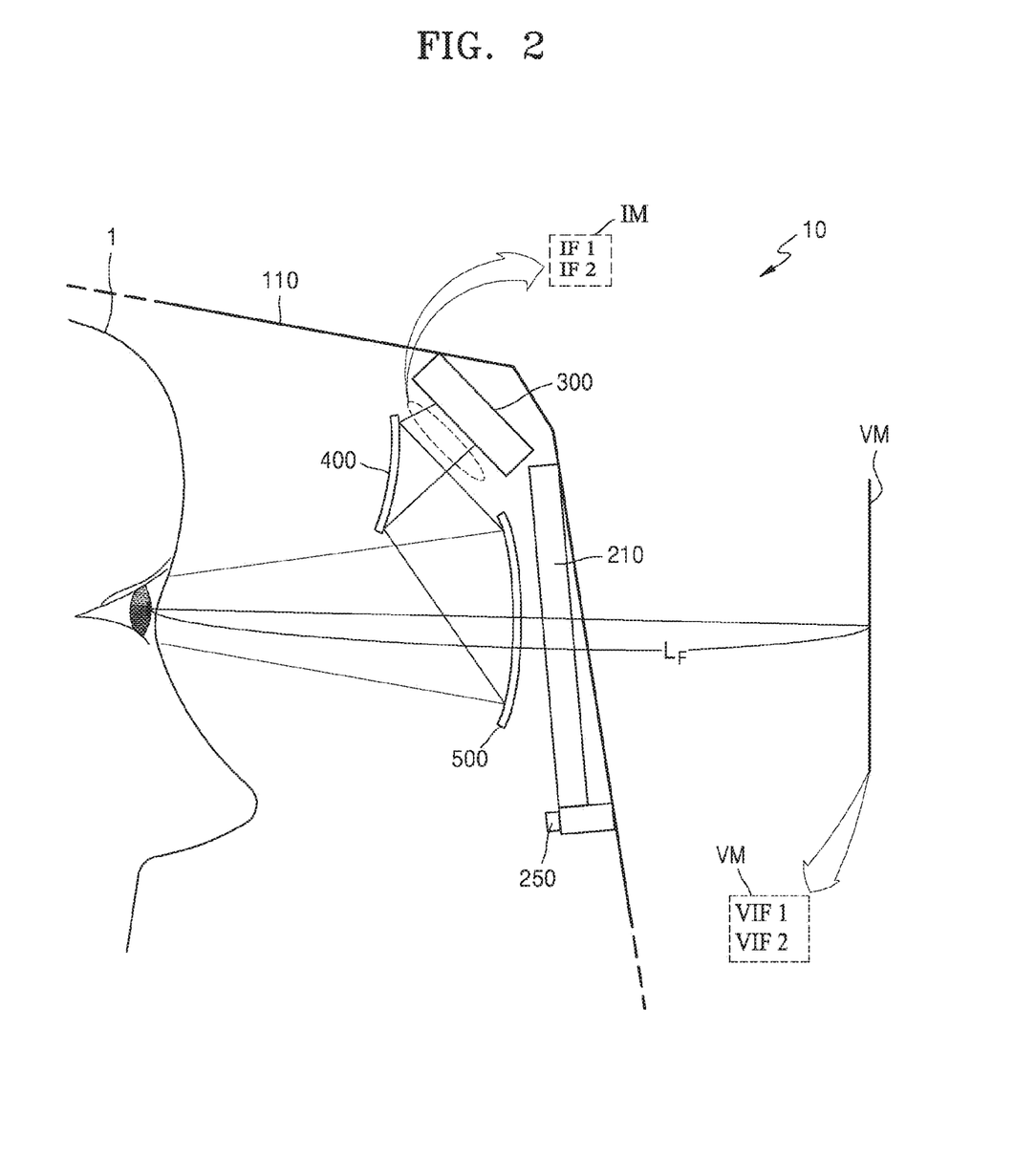
FIG. 2 is a side view, partly in section, of a protector for a welder according to an embodiment.

FIG. 2 is a side view, partly in section, of the protector 10 for a welder according to an embodiment.

Referring to FIG. 2, an image generator 300, an optical path bender 400, and a combiner 500 may be arranged in the main body 110. The image generator 300, the optical path bender 400, and the combiner 500 may be coupled to an internal side of the main body 110.

The image generator 300 generates an image having predetermined information (hereinafter, referred to as an initial image IM). The initial image IM is generated and emitted from the image generator 300 in the form of a beam having a predetermined divergence angle.

As an embodiment, the image generator 300 may include a transmissive display apparatus such as an LCD including a backlight, a thin film transistor, and liquid crystal (LC), etc. As another embodiment, the image generator 300 may include a self-emissive display apparatus such as an organic electroluminescence (EL) display or an inorganic EL display, or may include a reflective display apparatus such as a digital light processing (DLP), a liquid crystal on silicon (LCOS), etc.

The initial image IM may include pieces of information IF1 and IF2 about the welding. The pieces of information IF1 and IF2 about the welding may include information based on at least one of information about welding electric power and information about a welding wire, etc. The information about electric power used in the welding operation is provided from a welding apparatus (not shown) used by an operator 1, and may include information about a voltage and/or an electric current. The information about the welding wire is provided from the welding apparatus, and may include information about a feeding speed of the wire, and/or tension of the wire, etc. The controller may be arranged on the main body 110. For example, the controller may be fixedly arranged on an internal side or an external side of the main body 110.

The pieces of information IF1 and IF2 about the welding included in the initial image IM may be represented as numbers. For example, the image generator 300 may generate the initial image IM in which numerical values about a welding voltage, a welding current, a feeding speed of the wire, a tension of the wire, etc. are directly indicated. Alternatively, the pieces of information IF1 and IF2 about the welding included in the initial image IM may be represented as figures (e.g., a circle, an oval, a polygon, etc.) having predetermined colors, or as bars indicating degrees by using predetermined colors. The image generator 300 may generate the initial image IM, in which whether the welding voltage, the welding current, the feeding speed of the wire, the tension of the wire, etc. exceed a reference range is represented as a figure having a predetermined color such as red or green. According to an embodiment, the red color may denote an abnormal state and the green color may denote a normal state.

When the operator 1 wears the protector 10, an internal space between the main surface (or front portion), which covers a face of the operator 1, of the main body 110 and the face of the operator 1 is very narrow, and thus, the image generator 300 may be arranged adjacent to the internal surface of the front portion of the main body 110, as shown in FIG. 2. For example, the image generator 300 may be arranged on a space between an upper facial portion (around forehead) of the operator 1 and the internal surface of the front portion of the main body 110.

As an embodiment, a light exit surface of the image generator 300, e.g., a surface from which the initial image IM is emitted, may be arranged facing the operator 1, and the optical path bender 400 refracts the initial image IM towards the front portion of the main body 110. Thus, the narrow space between the front portion of the main body 110 and the face (e.g., forehead) of the operator 1 may be effectively used. The optical path bender 400 may include a reflector such as a reflective mirror. Alternatively, the optical path bender 400 may include an optical fiber, etc. In FIG. 2, the optical path bender 400 includes a reflective mirror having a convex surface towards the darkening filter 210.

Light of the initial image IM emitted from the image generator 300 proceeds towards the combiner 500 after being bent by the optical path bender 400. The combiner 500 may be arranged adjacent to the darkening filter 210. The combiner 500 may be arranged to overlap at least partially with the darkening filter 210. The combiner 500 may generate a virtual image VM on an outer portion of the main body 110 by projecting the light of the initial image IM that is incident thereto after being bent by the optical path bender 400.

The operator 1 may visually check pieces of information VIF1 and VIF2 about the welding via the virtual image VM. The pieces of information VIF1 and VIF2 about the welding included in the virtual image VM are identical with the pieces of information IF1 and IF2 about the welding included in the initial image IM. The virtual image VM may be placed at a first distance LF from the eye of the operator 1, and the first distance LF may be selected within a range from about 10 cm to about 1 m. A size of the virtual image VM may be greater than that of the initial image IM, for example, a magnification of the virtual image VM with respect to the initial image IM may be about 1.1 to 20.

The combiner 500 has a concave shape, and a concave surface may face the operator 1. The combiner 500 may have an aspherical surface. When the combiner 500 having the aspherical surface is used, generation of distortion while expanding the magnification may be reduced or prevented.

The protector 10 for the welder according to the embodiment of the present disclosure may provide the operator 1 with an actual image of the welding process, or provide the operator 1 with the virtual image VM generated by using the image generator 300, the optical path bender 400, and the combiner 500 together with the actual image, according to a mode. Hereinafter, an actual mode and an augmented reality mode will be described below with reference to FIGS. 3A to 3D.

Figure 3A:
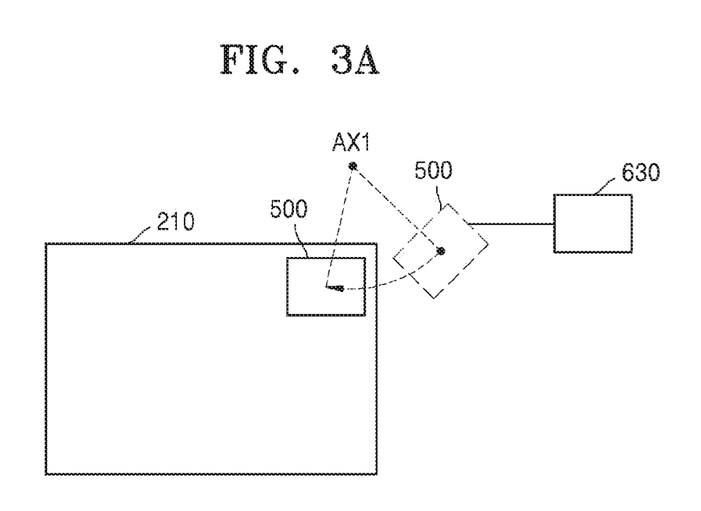
FIGS. 3A to 3C respectively illustrates placement between a darkening filter and a combiner according to an embodiment.
Figure 3B:
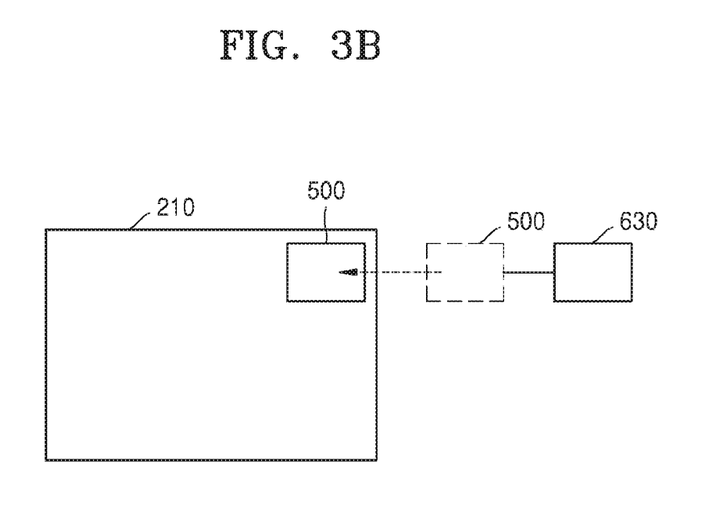
Figure 3C:
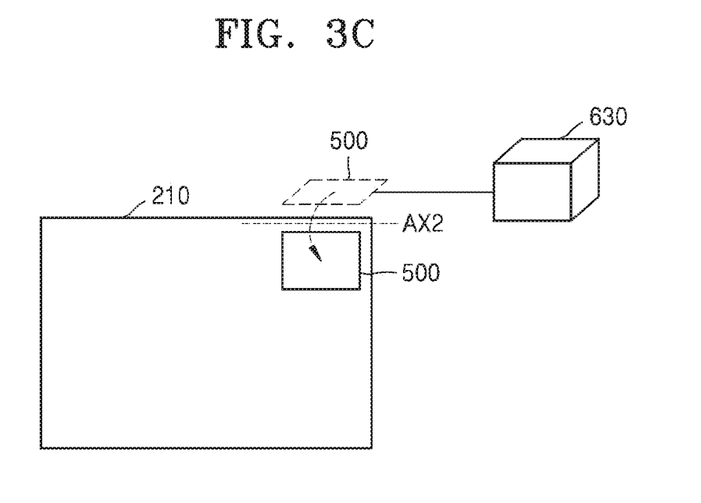
Figure 3D:
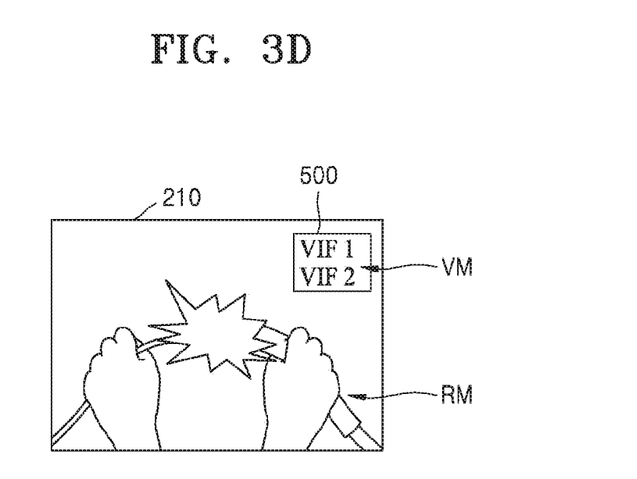
FIG. 3D is an image which is visible to a welder in an augmented reality mode.

FIGS. 3A to 3C respectively illustrates placement between a darkening filter and a combiner according to an embodiment, and FIG. 3D is an image which is visible to a welder in an augmented reality mode FIG. 3A shows relative positions of the darkening filter 210 and the combiner 500 in an actual mode and in an augmented reality mode according to an embodiment, FIGS. 3B and 3C respectively show relative positions of the darkening filter 210 and the combiner 500 in an augmented reality mode according to another embodiment, and FIG. 3D shows a screen displayed to the operator 1 in the augmented reality mode.

Referring to FIG. 3A, a position of the combiner 500 with respect to the darkening filter 210 may vary in a first mode (hereinafter, referred to as actual mode) and in a second mode (hereinafter, referred to as augmented reality mode).

In the actual mode (refer to a dotted line of FIG. 3A), the combiner 500 may be arranged adjacent to the darkening filter 210, but might not overlap with the darkening filter 210.

In the augmented reality mode (refer to a solid line of FIG. 3A), the combiner 500 may overlap with the darkening filter 210 according to an operation of a combiner mover 630 connected to the combiner 500. As an embodiment of the present disclosure, the combiner mover 630 may include a small-sized motor or a gear rotating about a predetermined axis, and the combiner 500 may be moved to at least partially overlap with the darkening filter 210, for example, with a corner portion of the darkening filter 210, according to the driving of the small-sized motor. FIG. 3A shows an example, in which the combiner 500 only overlaps with a part of the darkening filter 210 because the combiner 500 has a smaller size than that of the darkening filter 210.

In FIG. 3A, a case in which the combiner 500 is rotated about a predetermined axis AX1 by the combiner mover 630 to overlap with a part of the darkening filter 210 is described, but the present disclosure is not limited thereto.

As another embodiment, referring to FIG. 3B, the combiner 500 may be linearly moved in a direction by a small-sized motor, a cylinder, or a linear gear included in the combiner mover 630 to overlap with a part of the darkening filter 210.

As another embodiment, referring to FIG. 3C, the combiner 500 is arranged so that a main surface of the combiner 500 forms a predetermined angle with respect to a main surface of the darkening filter 210, and then, the combiner 500 is rotated about an axis AX2 that is in parallel with a side of the combiner 500 by the combiner mover 630 to overlap with a part of the darkening filter 210.

In the augmented reality mode in which the combiner 500 is arranged to overlap with a part of the darkening filter 210, the operator 1 may visually recognize an actual work image RM through the darkening filter 210, and may visually recognize the pieces of information VIF1 and VIF2 about the welding displayed in the virtual image VM through the combiner 500, as shown in FIG. 3D. Since the combiner 500 has a (semi-) transparent property, the combiner 500 may provide the operator 1 with the actual work image RM incident through the darkening filter 210, as well as the pieces of information VIF1 and VIF2 about the welding.

Figure 4:
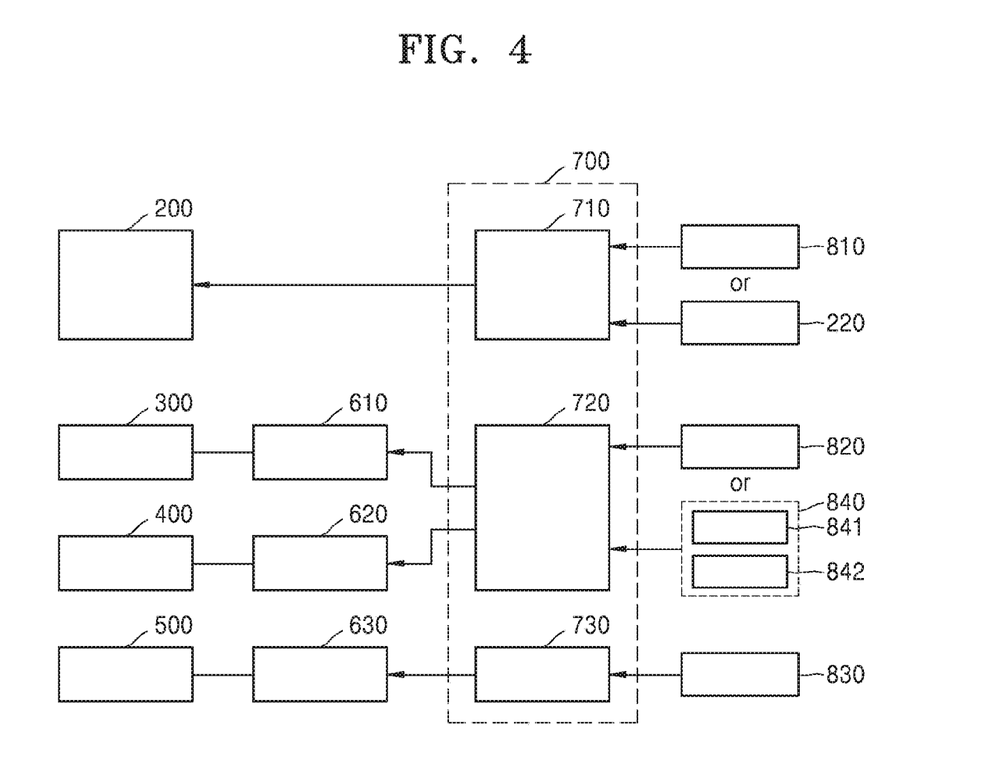
FIG. 4 is a schematic diagram showing a part in a protector for a welder according to an embodiment.
Figure 5A:
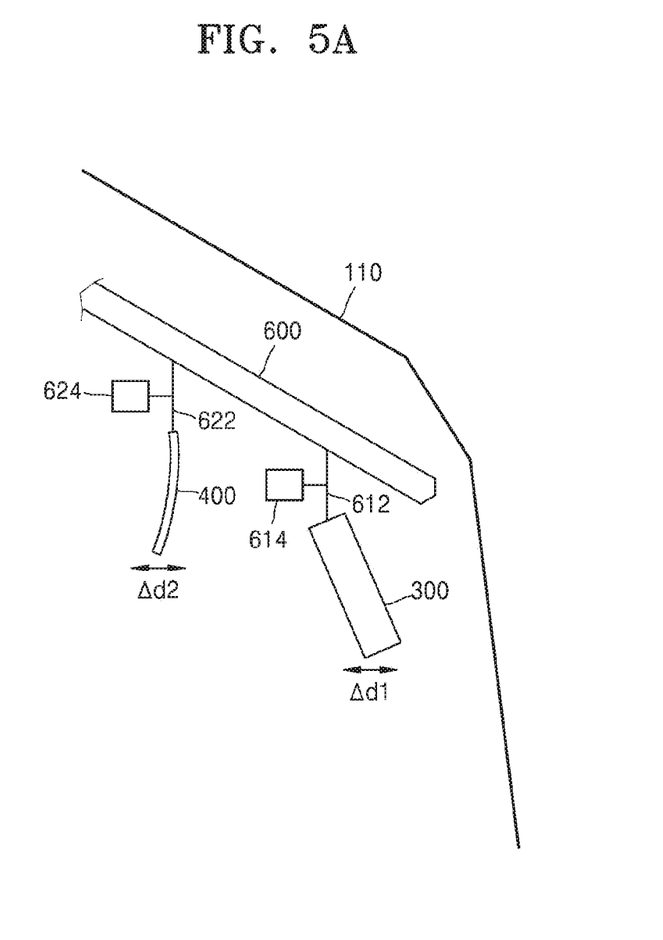
FIGS. 5A and 5B are side views, partly in section, showing a part of a protector for a welder.
Figure 5B:
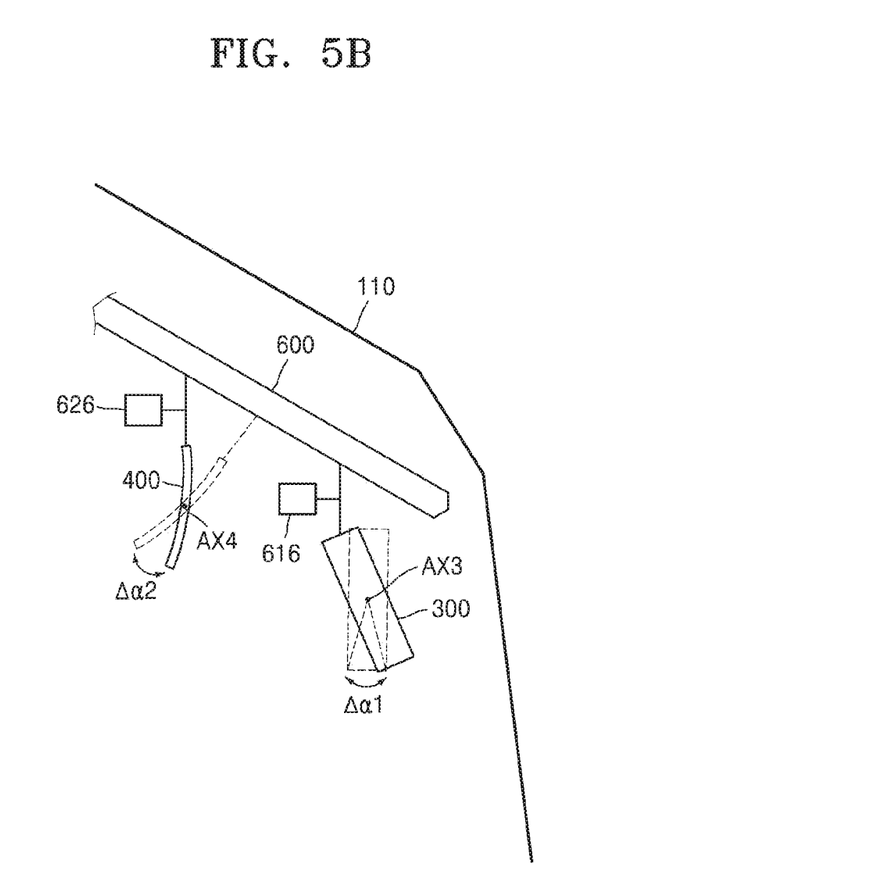

FIG. 4 is a block diagram partially showing the protector for welder according to the embodiment, and FIGS. 5A and 5B are side views, partly in section, showing a part of the protector for the welder.

Referring to FIG. 4, a first controller 710 may control a darkness of the darkening filter 210. The darkness control of the first controller 710 may be performed based on a selection (request) of the operator, e.g., when the operator manipulates a first manipulator 810 arranged on an outer side of the protector 10 (manual mode). The first manipulator 810 is a button type or a dial type, and may be located on the outer side of the protector 10, where the operator may easily manipulate. Alternatively, the darkness control of the first controller 710 may be performed based on an intensity of the welding light without the selection (request) of the operator (automatic mode). For example, when the first optical sensor 220 that is described above with reference to FIG. 1 senses a strong intensity of the welding light and provides the first controller 710 with an electric signal about the sensed intensity of the welding light, the first controller 710 may control the darkness of the darkening filter 210 based on the electric signal.

A second controller 720 may control at least one of the image generator 300 and the optical path bender 400, and a third controller 730 may control the combiner 500. For example, when the user (operator) operates a third manipulator 830 for selecting the augmented reality mode, the third controller 730 receives a signal from the third manipulator 830 and controls the combiner mover 630 to change a location of the combiner 500. The third manipulator 830 is a button type or a dial type, and may be located on the outer side of the protector 10, where the operator may easily manipulate. Variation in the location of the combiner 500 according to the control of the combiner mover 630 is described above with reference to FIGS. 3A to 3C, and hereinafter, controlling of the image generator 300 and the optical path bender 400 will be described.

The second controller 720 may move at least one of the image generator 300 and the optical path bender 400. By moving at least one of the image generator 300 and the optical path bender 400, a clear virtual image VM (see FIG. 2) may be provided according to a focal distance of the eyes of the operator. For example, a location of at least one of the image generator 300 and the optical path bender 400 may be controlled by the second controller 720 receiving a manipulation signal from the second manipulator 820. The second controller 720 may increase or decrease an optical distance from the image generator 300 to the combiner 500 by moving at least one of the image generator 300 and the optical path bender 400, and accordingly, the location of the virtual image VM (see FIG. 2) may vary and a high quality virtual image VM may be provided to the eyes of the operator. The location of the virtual image VM changed by the second controller 720 may vary within the range of the first distance LF described above.

According to an embodiment, at least one of the image generator 300 and the optical path bender 400 is linearly moved by a mover to change its location. As shown in FIGS. 4 and 5A, the image generator 300 may be moved in the protector 10 by a first mover 610 coupled to the image generator 300, and the optical path bender 400 may be moved in the protector 10 by a second mover 620 coupled to the optical path bender 400.

The first and second movers 610 and 620 may be each controlled according to a control signal generated by the second controller 720, and may include a moving rail 600 of a rail shape or small-sized motors 614 and 624 provided in the main body 110.

When the small-sized motor 614 provided in the main body 110 drives according to a signal from the second controller 720, a rail mover 612 moves on the rail 600 to linearly move the image generator 300 connected to the rail mover 612. Likewise, when the small-sized motor 624 drives according to a signal from the second controller 720, a rail mover 622 moves on the rail 600 so that the optical path bender 400 connected to the rail mover 622 linearly moves to change its location. A displacement $\Delta d1$ of the image generator 300 and a displacement $\Delta d2$ of the optical path bender 400 may be respectively selected within a range of about 0.2 cm to about 10 cm, a range of about 1 cm to about 10 cm, or a range of about 0.3 cm to about 5 cm, taking into account an internal space of the protector 10, but the present disclosure is not limited thereto.

As another embodiment, at least one of the image generator 300 and the optical path bender 400 may be rotated and dislocated by a mover. As shown in FIG. 5B, the image generator 300 and the optical path bender 400 may be rotated about predetermined axes AX3 and AX4 by small-sized motors 616 and 626 driven by the second controller 720. A rotary angle $\Delta\alpha1$ of the image generator 300 and a rotary angle $\Delta\alpha2$ of the optical path bender 400 may be both selected within an acute angle range.

In the above embodiment, the linear movement illustrated with reference to FIG. 5A and the rotary movement illustrated with reference to FIG. 5B are separately performed, but the present disclosure is not limited thereto. As another embodiment, the linear movement and the rotary movement of the image generator 300 and/or the optical path bender 400 may be performed together.

The dislocation of the image generator 300 and/or the optical path bender 400 controlled by the second controller 720, which is described above with reference to FIGS. 4 to 5B, might not be based on the manipulation signal generated when the user (operator) manipulates the second manipulator 820. For example, when the operator (hereinafter, referred to as a first operator) pushes a first setting button 841 after changing the location of the image generator 300 and/or the optical path bender 400 by manipulating the second manipulator 820, location information of the image generator 300 and/or the optical path bender 400 may be stored in a memory included in the second controller 720, and after that, location of the image generator 300 and/or the optical path bender 400 may be set only with the first operator's operation of pushing the first setting button 841. In FIG. 4, a setting button portion 840 includes two setting buttons, e.g., first and second setting buttons 841 and 842, but the number of setting buttons may vary.

Figure 6:
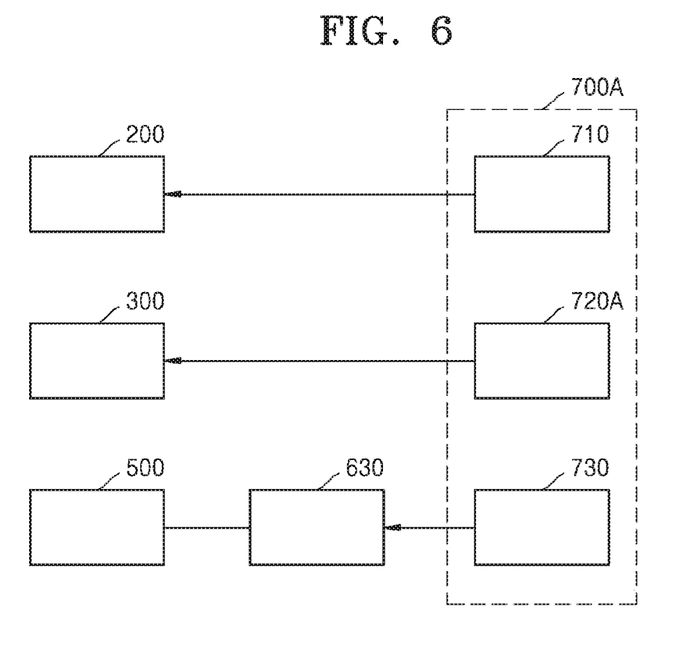
FIG. 6 is a block diagram showing a part in a protector for a welder according to an embodiment.

FIG. 6 is a block diagram partially showing a protector for a welder according to an embodiment.

Referring to FIG. 6, a controller 700A includes first to third controllers 710, 720A, and 730, and operations of the first and third controllers 710 and 730 are described above. Thus, operations of the second controller 720A will be described hereinafter.

Unlike the above embodiment illustrated with reference to FIGS. 4 to 5C, the protector for welder according to the current embodiment may provide a virtual image VM of high quality to the eyes of the operator by adjusting a location of the virtual image VM, when the second controller 720A directly controls an initial image IM (see FIG. 2) of the image generator 300 without changing the locations of the image generator 300 and the optical path bender 400.

For example, the second controller 720A may adjust the location of the virtual image VM by controlling a size of the initial image IM of the image generator 300. Since the size of the initial image IM is changed, the divergence angle of the initial image IM varies, and thus, the virtual image VM may be arranged to be suitable for the eyes of the operator.

The controller 700A may compensate for distortion of the virtual image VM (see FIG. 2). For example, the second controller 720A may compensate for the distortion of the virtual image VM by reducing a width of the initial image IM of the image generator 300 in a longitudinal direction (height).

According to the embodiments illustrated with reference to FIGS. 4 and 6, the controller 700 or 700A includes three controllers, but the present disclosure is not limited thereto. As another embodiment, since the darkening filter 210, the image generator 300, the optical path bender 400, and the combiner 500 may be controlled by one controller or a plurality of controllers, the number of controllers is not limited.

Figure 7:
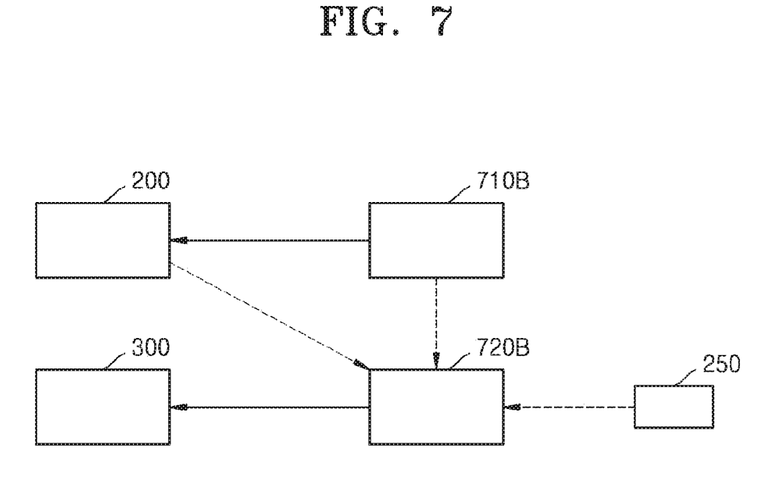
FIG. 7 is a block diagram showing a part in a protector for a welder according to an embodiment.

FIG. 7 is a block diagram partially showing a protector for a welder according to an embodiment. In FIG. 7, a third controller is omitted for convenience of description.

According to the embodiment, a brightness (lightness) of the virtual image VM (see FIG. 2) provided to the operator in an augmented reality mode may be adjusted. For example, a second controller 720B may adjust the brightness of the virtual image VM by controlling brightness of the initial image IM based on a darkness of the darkening filter 210.

As shown in FIG. 2, a second optical sensor 250 may be arranged in the main body 110. In FIG. 2, the second optical sensor 250 is arranged around the darkening filter 210.

Brightness in the main body 110 varies depending on the darkness of the darkening filter 210, and the second optical sensor 250 may generate a signal regarding the brightness in the main body 110. The signal generated by the second optical sensor 250 is transferred to the second controller 720B, and the second controller 720B may control the brightness of the image generator 300 based on the signal. Since the brightness of the virtual image VM depends upon the brightness of the image generator 300, e.g., the brightness of the initial image IM, the brightness of the virtual image VM may be adjusted through the above control operations.

As another embodiment, the brightness control of the virtual image VM based on the darkness of the darkening filter 210 may be performed without using an illuminance sensor. For example, the second controller 720B may directly receive a signal regarding the darkness from the darkening filter 210 or a first controller 710B, and may control the brightness of the image generator 300 based on the signal. In this case, the initial image IM of the image generator 300 may be emitted with its brightness adjusted based on the received signal, and accordingly, the brightness of the virtual image VM may be adjusted.

As described in the above embodiments, since the brightness of the virtual image VM is adjusted based on the darkness of the darkening filter 210, the operator may identify information included in the virtual image VM without experiencing glare.

The brightness control of the virtual image VM based on the darkness of the darkening filter 210 described above with reference to FIG. 7 may be also applied to the protector for welder according to the embodiments illustrated with FIGS. 4 and 6.

Figure 8:
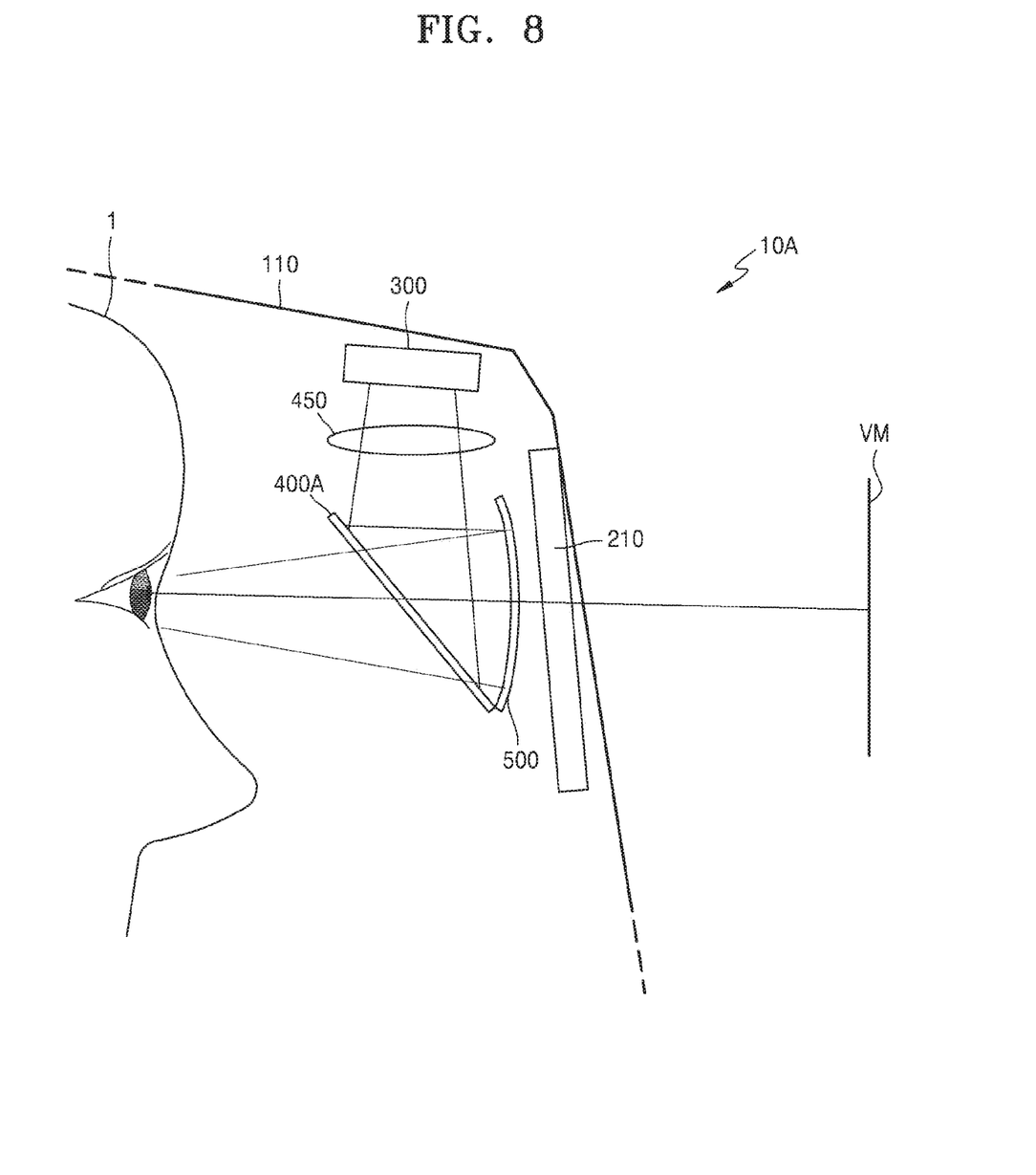
FIG. 8 is a side view, partly in section, of a protector for a welder according to an embodiment.

FIG. 8 is a side view, partly in section, of a protector 10A for a welder according to an embodiment.

The protector 10A for welder illustrated in FIG. 8 is different from the protector 10 described above with reference to FIG. 2 in view of including an optical path bender 400A having a reflector such as a semi-transparent mirror and further including a lens unit 450, but other components and operations are the same as those illustrated with reference to FIGS. 2 to 6, and thus, detailed descriptions are omitted.

The protector for welder according to the above embodiments may easily provide visual information that is necessary for the welding operation of the operator, and thus, the operator may check the information, as well as an actual work, and the operating efficiency may be improved.

It should be understood that embodiments described herein are considered in a descriptive sense only and not for purposes of limitation. Descriptions of features or aspects within each embodiment should be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A protector for a welder, the protector comprising:
    a main body configured to cover a face and eyes of an operator;
    a darkening filter arranged in a front side of the main body and configured to protect the eyes of the operator;
    an image generator arranged in the main body and configured to generate image light;
    an optical path bender configured to change a proceeding path of the image light; and
    a combiner configured to generate a virtual image on an outer portion of the main body by projecting the image light, and arranged adjacent to the darkening filter; and
    a combiner mover configured to move the combiner, so that the combiner is located in the main body without overlapping with the darkening filter in a first mode and the combiner overlaps with at least a part of the darkening filter in a second mode.

2. The protector of claim 1, wherein the optical path bender comprises at least one of a reflective mirror, a semi-transmissive mirror, and optical fiber.

3. The protector of claim 1, wherein the virtual image represents information based on at least one of information about electric power used during a welding operation or information about a welding wire.

4. The protector of claim 1, further comprising a controller configured to control a location of the virtual image.

5. The protector of claim 4, wherein the controller is configured to control the location of the virtual image by changing a location of at least one of the image generator or the optical path bender.

6. The protector of claim 5, further comprising a mover configured to move the location of at least one of the image generator or the optical path bender.

7. The protector of claim 4, wherein the controller is configured to control the location of the virtual image based on a size of an image generated by the image generator.

8. The protector of claim 1, wherein the virtual image has a brightness that is based on a darkness of the darkening filter or a brightness inside the main body.

9. The protector of claim 8, further comprising an optical sensor arranged in the main body.

* * * * *